United States Patent
Takahashi et al.

(10) Patent No.: US 7,579,608 B2
(45) Date of Patent: Aug. 25, 2009

(54) PARTICLE-BEAM TREATMENT SYSTEM

(75) Inventors: Osamu Takahashi, Tokyo (JP); Yuehu Pu, Tokyo (JP); Hisashi Harada, Tokyo (JP); Masahiro Ikeda, Tokyo (JP); Yasuyuki Takatani, Tokyo (JP); Hiroshi Otani, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 173 days.

(21) Appl. No.: 11/870,512

(22) Filed: Oct. 11, 2007

(65) Prior Publication Data

US 2008/0298553 A1    Dec. 4, 2008

(30) Foreign Application Priority Data

Jun. 1, 2007    (JP)    ............... 2007-146988

(51) Int. Cl.
G21K 5/04    (2006.01)
(52) U.S. Cl. .................. 250/492.3; 378/152
(58) Field of Classification Search ............. 250/492.3; 378/152, 206
See application file for complete search history.

(56) References Cited

U.S. PATENT DOCUMENTS

| 4,868,843 | A | * | 9/1989 | Nunan ........................ 378/152 |
| 4,882,741 | A |   | 11/1989 | Brown |
| 5,039,867 | A | * | 8/1991 | Nishihara et al. ........ 250/492.3 |
| 5,757,881 | A |   | 5/1998 | Hughes |
| 6,218,675 | B1 | * | 4/2001 | Akiyama et al. ......... 250/492.3 |
| 2004/0013237 | A1 |   | 1/2004 | Brown et al. |
| 2004/0188645 | A1 |   | 9/2004 | Arakawa |

FOREIGN PATENT DOCUMENTS

DE    39 00 884    7/1990

(Continued)

OTHER PUBLICATIONS

Notification of Reasons for Refusal in JP 2007-146988 dated Jan. 20, 2009, and an English Translation thereof.

(Continued)

*Primary Examiner*—Kiet T Nguyen
(74) *Attorney, Agent, or Firm*—Buchanan Ingersoll & Rooney PC

(57) ABSTRACT

Provision is made for a particle-beam treatment system in which, even during particle-beam irradiation, the shape of a multileaf collimator is monitored. The particle-beam treatment system, in which multi-layer conformal irradiation is performed while the setting of the shape of the multileaf collimator in an irradiation head is changed during particle-beam irradiation, is provided with an optical shape-monitoring unit mounted attachably and detachably in the snout portion at the downstream side of the multileaf collimator, the optical shape-monitoring unit having a shape-monitoring mirror, opposing the multileaf collimator, for monitoring the shape of the multileaf collimator; a video camera for shooting the multileaf-collimator shape reflected by the shape-monitoring mirror; and an image monitor for displaying an image of the video camera that shoots the shape of the multileaf collimator.

9 Claims, 9 Drawing Sheets

FOREIGN PATENT DOCUMENTS

| | | |
|---|---|---|
| EP | 0 193 509 | 9/1986 |
| GB | 2 211 710 A | 7/1989 |
| JP | 1-146564 A | 6/1989 |
| JP | 1-146565 A | 6/1989 |
| JP | 1-274741 A | 11/1989 |
| JP | 2-182273 A | 7/1990 |
| JP | 6-246015 A | 9/1994 |
| JP | 2004-097471 | 4/2004 |
| JP | 2004-290242 | 10/2004 |
| JP | 2004-321502 | 11/2004 |

OTHER PUBLICATIONS

Nobuyuki Kanematsu et al., "Improvement of the HIMAC Treatment System with the Layer-Stacking Conformal Irradiation Method," Physics Annual Report 2001-2002, Chapter 4 (cited in present application on p. 6).

Office Action in corresponding German Application No. 10 2008 004 448.8-54 dated Feb. 16, 2009, and an English Translation thereof.

* cited by examiner

29a: PATIENT-POSITION INFORMATION UPON START OF IRRADIATION/DEVICE SETTING INFORMATION
29b: PATIENT-POSITION INFORMATION UPON CUTOFF OF IRRADIATION/DEVICE SETTING INFORMATION

PARTICLE-BEAM TREATMENT SYSTEM

BACKGROUND OF THE INVENTION

1. Field of the Invention

The present invention relates to a particle-beam treatment system in which, in the case where, during particle-beam irradiation, multi-layer conformal irradiation is performed while setting of the shape (leaf position) of a multileaf collimator in an irradiation head is changed, the shape of the multileaf collimator is detected by a leaf-position detection mechanism, and more particularly to a particle-beam treatment system in which, during particle-beam irradiation, the shape of the multileaf collimator can be monitored.

2. Description of the Related Art

In a particle-beam treatment system that performs multi-layer conformal irradiation, the dose to be administered to a patient and the distribution thereof are spatially divided and then delivered, so that the dose delivery is made optimal for the shape of a target. The dose distribution divided and delivered in this manner depends on the setting of the irradiation system, such as setting of the shape of the multileaf collimator and the like, and the setting condition of the patient position. In the case where, during particle-beam irradiation, the shape of the multileaf collimator or the patient position is changed from the shape or the setting position that have been decided in a treatment plan, the dose to be administered and the dose distribution differ from those in the treatment plan; therefore, it is required to immediately stop the particle-beam irradiation. For this reason, the monitoring (ascertainment) of the shape (leaf position) of the multileaf collimator and the patient position is an important function for delivering to the patient the dose distribution that has been prescribed in a treatment plan; thus, redundancy and multiplicity are required in the foregoing monitoring.

In the case where, in a particle-beam treatment, a static irradiation, which has been practiced since the time before the advent of the multi-layer conformal irradiation, was performed, the shape of the multileaf collimator was ascertained immediately prior to the particle-beam irradiation, based on a light-irradiation field, formed by a light localizer, and X-ray radiographing; then, it could be secured, through detection by use of a detector incorporated in the multileaf collimator, that the forgoing shapes did not change during irradiation. In addition, the conventional monitoring and ascertainment of a patient position were visually performed by shooting a marker written on the surface of the patient body and the projected image of a laser pointer, through a video camera mounted on the ceiling or the sidewall of the treatment room.

FIG. 8 is a conventional system block diagram illustrating a method of monitoring and ascertaining the shape of a multileaf collimator and a patient position in the case where a static irradiation, which has been practiced since the time before the advent of the multi-layer conformal irradiation, is performed. FIG. 9 is a configuration diagram illustrating the structure and the system of a typical multileaf collimator. In the conventional static particle-beam treatment, the ascertainment of the shape (leaf position) of a multileaf collimator has been performed by observing, immediately prior to the irradiation, the light-irradiation field formed by a light localizer 11 and the image, of a digital radiograph (DR) 19, which is radiographed, with a X-ray source 13 movably provided on the beam axis, in addition to automatic comparison performed by a leaf-position detection mechanism (e.g., the position is detected by use of an encoder) incorporated in the multileaf collimator. In some cases, a particle-beam flatness monitor is further utilized. In addition, the X-ray source 13 moves on a monitor drive stand 51 that is provided in such a way as to be separated from and to be on a multileaf collimator 14; thus, the X-ray source 13 can be disposed on the beam axis.

Explanations therefor will be made with reference to FIGS. 8 and 9. In FIG. 8, reference characters 1, 2, 2a, 2b, 3, 4, 5, and 6 denote an irradiation head, a patient, a diseased site of the patient, a patient-position marker, a particle beam, a dose monitor, wobbler magnets, and a scatterer, respectively; reference characters 7, 8, 9, 10, 11, 12, 13, 14, and 14a denote a ridge filter, a range shifter, an irradiation-system control computer, an irradiation-head control device, a light localizer, a mirror, an X-ray source, a multileaf collimator, and a multi-leaf-collimator control device, respectively; reference characters 15, 16, 17a, 18, 19, 20, 20a, and 51 denote a patient-monitoring video camera, a video-camera controller, an image monitor, a treatment table, a DR, a laser pointer, a laser beam, and a monitor drive stand, respectively.

In FIG. 9, reference characters 14a, 14b, 21, 22, 23, 24, 25, 26, 27, and 28 denote a multileaf collimator control device, a multileaf collimator head unit, a shape of a multileaf collimator, a collimator leaf, a leaf drive mechanism, a mechanical stopper, a leaf-position detector, a leaf drive unit, a signal processing circuit, and a collimator manipulation unit, respectively. The particle beam 3 accelerated by a particle-beam accelerator is led by a beam transport system to the irradiation head 1, limited by the multileaf collimator 14 to a necessary irradiation region, and then irradiated onto the patient 2.

The ascertainment of the shape (leaf position) 21 of the multileaf collimator has been performed by, immediately prior to the irradiation, disposing the light localizer 11 and the mirror 12 at the upstream side of the multileaf collimator 14, thereby visually ascertaining the multileaf-collimator shape which is projected onto a plane perpendicular to the traveling direction of the particle beam, in addition to performing automatic comparison and ascertainment of the respective output information items of the position-detection mechanisms 25 for the corresponding collimator leaves and the original setting information in the treatment plan; furthermore, the shape 21, of the multileaf collimator, which is X-rayed with the X-ray digital radiograph (DR) 19 with the X-ray source 13 movably arranged on the beam line, has been ascertained. Additionally, in the conventional monitoring of a patient position, the patient-position marker 2b written on the surface of the patient body and the light marker (e.g., a cross line), which is obtained by projecting, onto the surface of the patient body, the laser beam 20a from the laser pointer 20 provided on the sidewall or the ceiling of the treatment room, have been shot by the video camera 15 that is also disposed on the sidewall or the ceiling of the treatment room and ascertained on the image monitor 17a. In addition, the technical literatures for this field include the following documents:

Patent Document 1: Japanese Patent Application Laid-Open No. 1989-274741

Patent Document 2: Japanese Patent Application Laid-Open No. 1990-182273

Patent Document 3: Japanese Patent Application Laid-Open No. 1994-246015

Patent Document 4: U.S. Pat. No. 4,882,741 (corresponding Japanese publication: Japanese Patent Application Laid-Open No. 1989-146564)

Patent Document 5: GB Patent No. 2,211,710A (corresponding Japanese publication: Japanese Patent Application Laid-Open No. 1989-146564)

Non-patent Document 1: PHYSICS Annual Report 2001-2002, 4. Improvement of the HIMAC Treatment System with the Layer-Stacking Conformal Irradiation Method, Nobuyuki Kanematsu, et al.

In a conventional static irradiation method utilizing a particle-beam treatment system, as illustrated in FIG. 8, the monitoring and the ascertainment of the shape of a multileaf collimator has been performed by visually ascertaining, immediately prior to irradiation, the light-irradiation field formed by the light localizer 11 and the mirror 12 that are disposed at the upstream side of the multileaf collimator and observing the image, of the digital radiograph (DR) 19, which is radiographed with the X-ray source 13 disposed on the beam axis, in addition to automatic comparison performed by leaf-position detection mechanisms incorporated in the multileaf collimator; however, because, the ascertainment work in a treatment room is involved, the foregoing methods, except for the method of ascertainment performed by the leaf-position detection mechanisms incorporated in the multileaf collimator, cannot be applied to a dynamic irradiation method such as the multi-layer conformal irradiation in which the setting for a multileaf collimator is changed during irradiation. Moreover, because the space above the monitor drive stand 51 is limited, it is difficult to provide additional reinforcement. Still moreover, the conventional monitoring of a patient position has been performed by shooting the marker 2b written on the surface of the patient body and the image of the laser pointer 20, through the video camera 15 mounted on the ceiling or the sidewall of the treatment room, thereby carrying out visual ascertainment on the image monitor 17a; however, in some cases, the monitoring subject has not securely been captured, depending on the irradiation arrangement.

It is possible in principle to make the leaf-position detector 25 multiple and redundantly ascertain the shape 21 of the multileaf collimator, in order to ascertain the setting condition during particle-beam irradiation; however, the multileaf collimator has a great number of drive elements and the space where the newly added leaf-position detectors and signal transmission paths are mounted in the multileaf collimator head unit is limited, whereby many difficult issues exist. Furthermore, in contrast to the conventional static irradiation method, in the multi-layer conformal irradiation, a dose is administered to a treatment target that is divided into a plurality of irradiation units; therefore, a change in the patient position during particle-beam irradiation forms high-dose and low-dose regions in the dose distribution.

The foregoing issue cannot be addressed with the setting margin, for the target, which is set in accordance with the conventional static irradiation method and in consideration of the change of the body position; thus, nothing but improvement in the fixing method for the fixing device and the like and more stringent monitoring of body-position change can serve as measures for the foregoing issue. In the conventional monitoring through the video camera 15 disposed on the sidewall or the ceiling of a treatment room, a dead angle or the like, which may be caused depending on the irradiation arrangement, may make it difficult to securely monitor the body position that is subject to irradiation.

SUMMARY OF THE INVENTION

The present invention has been implemented in order to solve the foregoing problems; the objective of the present invention is to obtain a particle-beam treatment system in which monitoring of the shape of a multileaf collimator can be performed even during particle-beam irradiation, and even in the case where, during particle-beam irradiation, the shape of the multileaf collimator is changed, redundant monitoring can be performed, in addition to monitoring of the shape of the multileaf collimator, through leaf-position detection mechanisms.

A particle-beam treatment system, according to the present invention, in which, in the case where, during particle-beam irradiation, multi-layer conformal irradiation is performed while setting of the shape of a multileaf collimator in an irradiation head is changed, the shape of the multileaf collimator is detected by a leaf-position detection mechanism, is provided with an optical shape-monitoring unit mounted attachably and detachably in the snout portion at the downstream side of the multileaf collimator, the optical shape-monitoring unit having a shape-monitoring mirror, opposing the multileaf collimator, for monitoring the shape of the multileaf collimator, a video camera for shooting the multileaf-collimator shape reflected by the shape-monitoring mirror, and an image monitor for displaying an image of the video camera that shoots the shape of the multileaf collimator; the particle-beam treatment system enables the shape of the multileaf collimator to be monitored during particle-beam irradiation.

According to a particle-beam treatment system of the present invention, monitoring of the shape of a multileaf collimator can be performed even during particle-beam irradiation, and even in the case where, during particle-beam irradiation, the shape of the multileaf collimator is changed, redundant monitoring can be performed, in addition to monitoring, through a leaf-position detection mechanism, of the shape of the multileaf collimator.

A particle-beam treatment system, according to the present invention, in which, in the case where, during particle-beam irradiation, multi-layer conformal irradiation is performed while setting of the shape of a multileaf collimator in an irradiation head is changed, the shape of the multileaf collimator is detected by leaf-position detection mechanisms, is provided with an optical shape-monitoring unit mounted attachably and detachably in the snout portion at the downstream side of the multileaf collimator, the optical shape-monitoring unit having a shape-monitoring mirror, opposing the multileaf collimator, for monitoring the shape of the multileaf collimator, a video camera for shooting the multileaf-collimator shape reflected by the shape-monitoring mirror, and a comparison means for comparing an image of the video camera with multileaf-collimator-shape information in a treatment plan and determining whether or not the comparison result is appropriate; the particle-beam treatment system performs particle-beam irradiation or particle-beam cutoff processing, depending on whether or not the comparison result is appropriate.

According to a particle-beam treatment system of the present invention, an image of the video camera that shoots the multileaf-collimator shape reflected by the shape-monitoring mirror and multileaf-collimator-shape information in a treatment plan are compared, and particle-beam irradiation or particle-beam cutoff processing is performed depending on whether or not the comparison result is appropriate; therefore, inappropriate particle-beam irradiation can be avoided.

The foregoing and other objects, features, aspects and advantages of the present invention will become more apparent from the following detailed description of the present invention when taken in conjunction with the accompanying drawings.

DETAILED DESCRIPTION OF THE INVENTION

Embodiment 1

Figure 1:
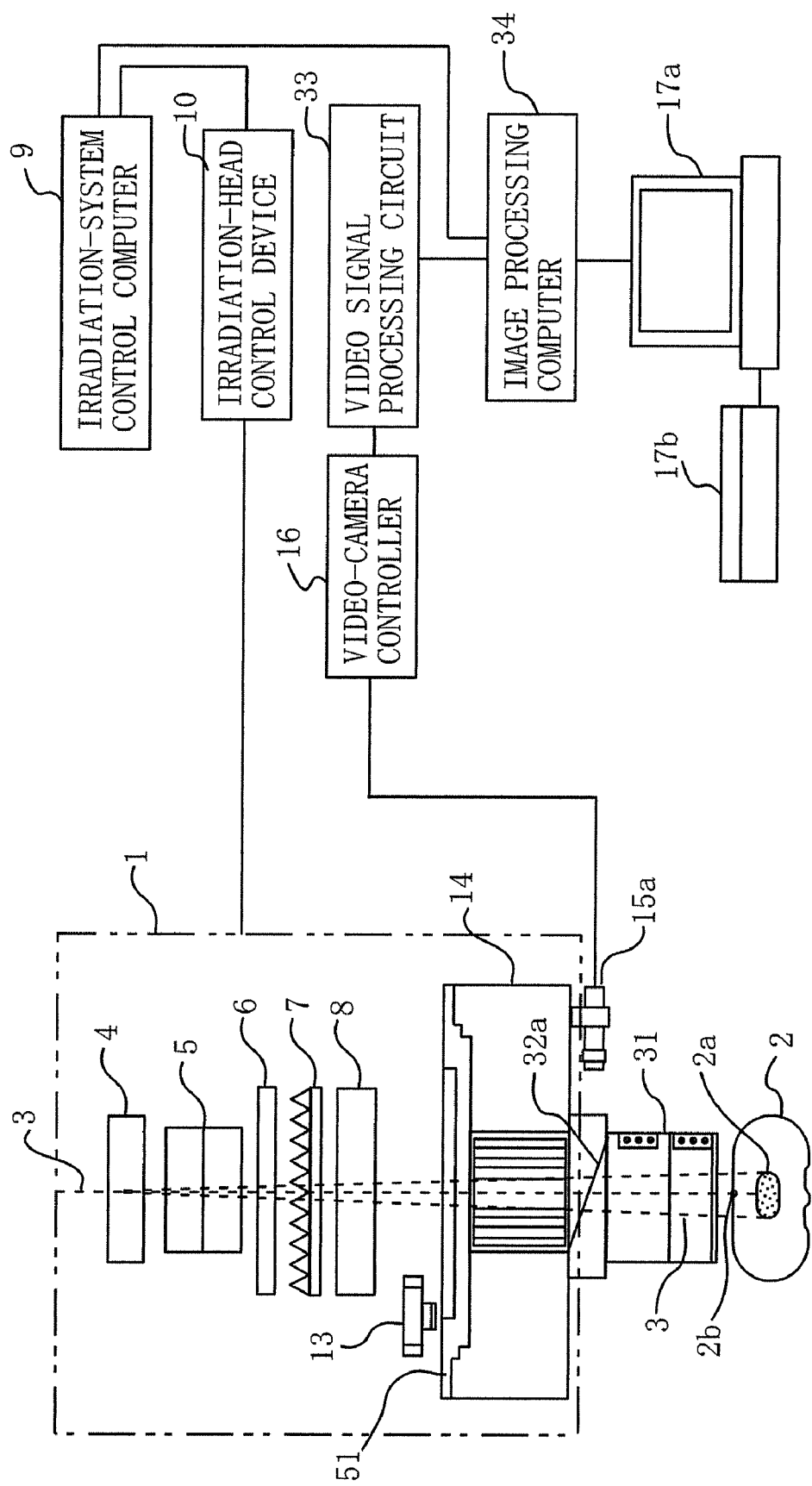
FIG. 1 is a system block diagram illustrating a particle-beam treatment system according to Embodiment 1 of the present invention.
Figure 2:
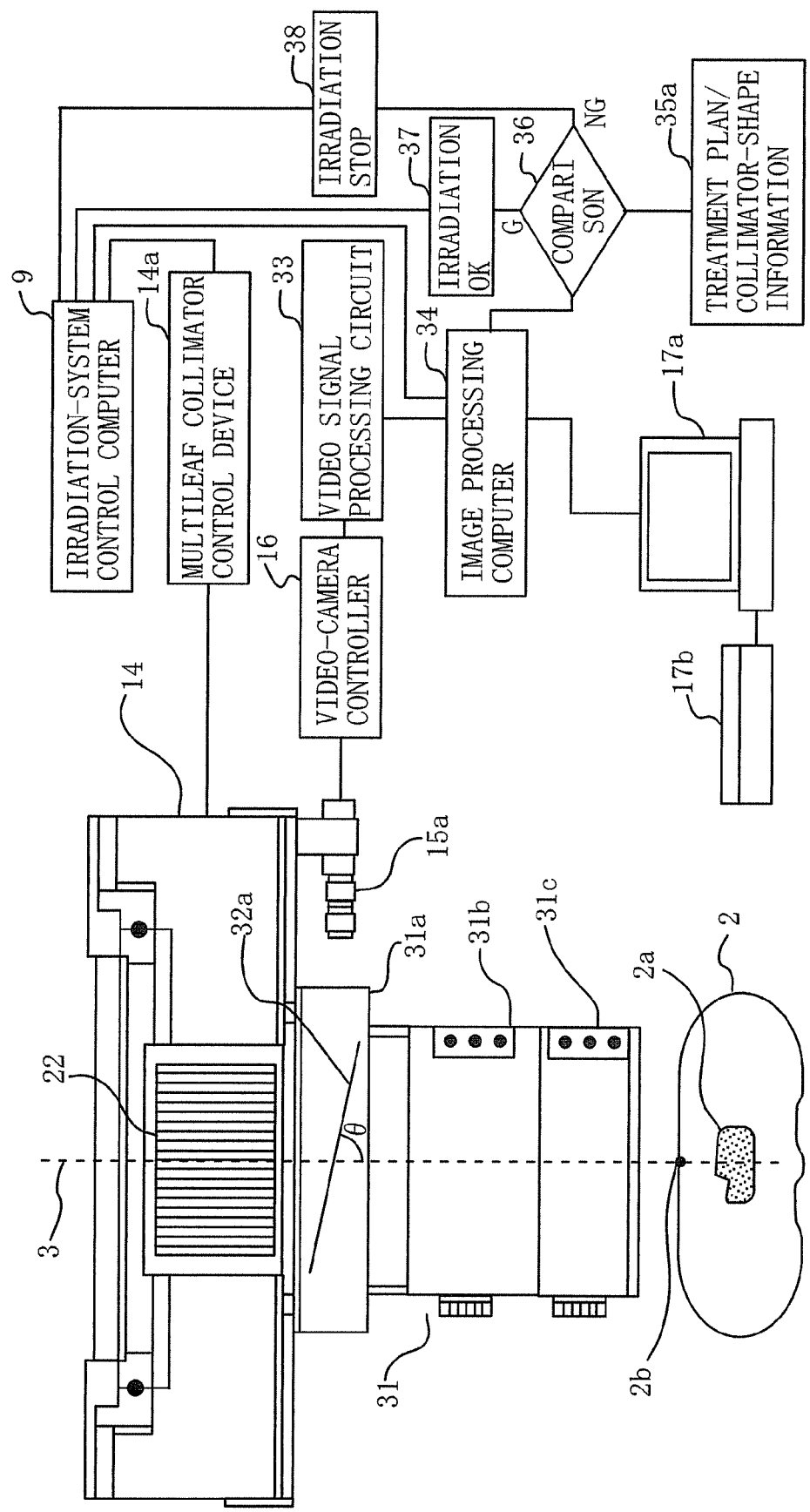
FIG. 2 is a system block diagram illustrating a multileaf collimator head unit and the control system therefor according to Embodiment 1.
Figure 3:
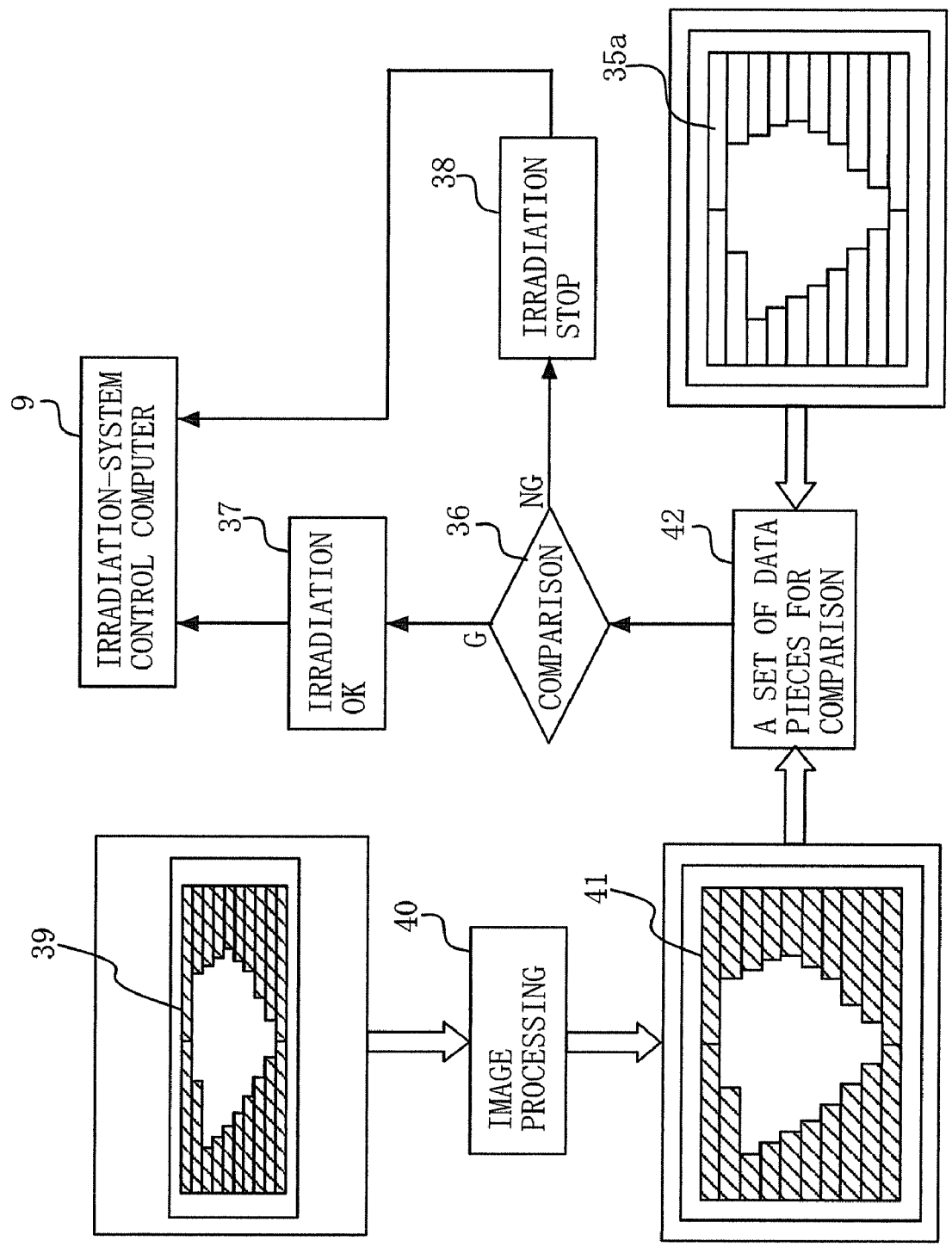
FIG. 3 is a flowchart representing a collimator-shape monitoring flow according to Embodiment 1.
Figure 9:
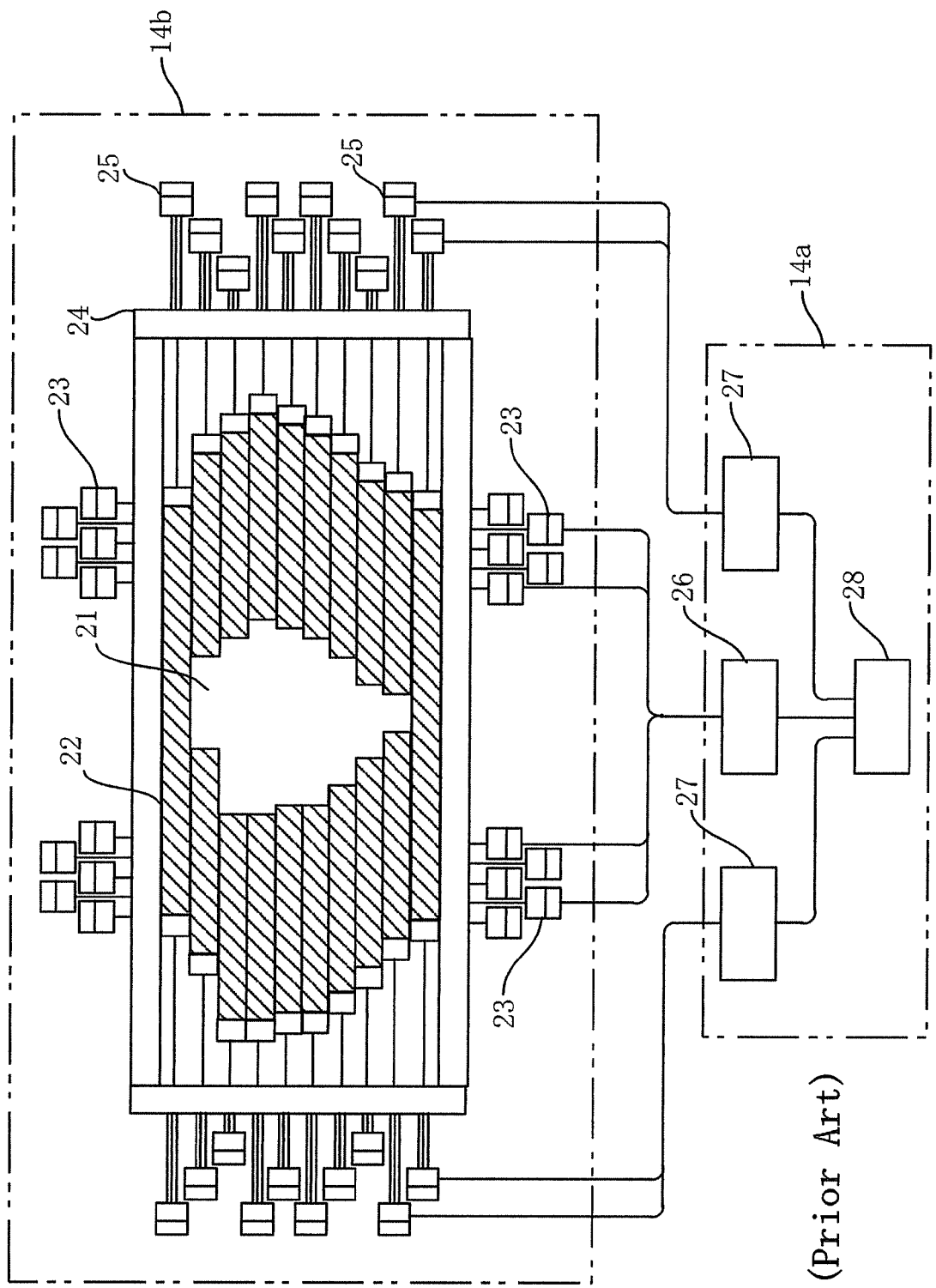
FIG. 9 is a configuration diagram illustrating the schematic shape and system of a typical multileaf collimator.

FIG. 1 is a system block diagram illustrating a particle-beam treatment system according to Embodiment 1 of the present invention. FIG. 1 illustrates principle constituent elements in a configuration in which an optical shape-monitoring unit, which includes a multileaf-collimator-shape monitoring mirror utilized in the multi-layer conformal irradiation, is mounted in an irradiation head. FIG. 2 is a system block diagram illustrating a multileaf collimator head unit and the control system therefor according to Embodiment 1. FIG. 3 is a flowchart representing a collimator-shape monitoring flow according to Embodiment 1. Meanwhile, the structure and the leaf-position detection mechanism of the typical multileaf collimator explained with reference to FIG. 9 can directly be applied to Embodiment 1; in the present specification, the same reference characters in the figures denote identical or corresponding parts; therefore, explanations therefor may be omitted.

In FIG. 1, reference characters 1, 2, 2a, 2b, 3, 4, 5, and 6 denote an irradiation head of a particle-beam treatment system, a patient, a diseased site of the patient, a patient-position marker, a particle beam, a dose monitor, wobbler magnets, and a scatterer such as Pb, respectively; reference characters 7, 8, 9, 10, 13, and 14 denote a ridge filter such as Al, a range shifter such as an acrylate resin, an irradiation-system control computer, an irradiation-head control device, an X-ray source, and a multileaf collimator, respectively; reference characters 15a, 16, 17a, 17b, 31, 32a, 33, and 34 denote a video camera, a video-camera controller, an image monitor, a keyboard, an optical shape-monitoring unit, a shape-monitoring mirror, a video signal processing circuit, and an image processing computer, respectively.

In FIG. 2, reference characters 14a, 22, 31a, 31b, 31c, 35a, 36, 37 and 38 denote a multileaf collimator control device, collimator leaves, a shape-monitoring-mirror mounting stand, a compensation filter mounting stand, a patient collimator mounting stand, collimator-shape information in a treatment plan, an image comparison means for a multileaf-collimator shape, an irradiation OK signal, and an irradiation stop signal or an irradiation prohibition signal, respectively. In FIG. 3, reference characters 35a, 39, 40, 41, and 42 denote collimator-shape information in a treatment plan, a collimator-shape raw image, image processing, an image corresponding to a direct view after the image processing, and a set of comparison-image data pieces.

Next, the operation of the particle-beam treatment system will be explained. In FIG. 1, the particle beam 3 accelerated by a particle-beam accelerator in the particle-beam treatment system enters the dose monitor 4 in irradiation head 1, by way of a beam transport system; in the dose monitor 4, the irradiation dose is counted. The wobbler magnets 5 and the scatterer 6 form the particle beam 3 whose irradiation field is enlarged. After exiting from the scatterer 6, the particle beam 3 passes through the ridge filter 7; the Bragg peak is enlarged in the depth direction and a homogeneous dose region is formed; then the range is adjusted by the range shifter 8.

In the multi-layer conformal irradiation, a spatial dose delivery is administered in such a way as to be divided in the depth direction; upon the initial irradiation, the wobbler magnets 5, the range shifter 8, and the multileaf collimator 14 (the multileaf-collimator shape) are set in accordance with the dose delivery at the deepest portion, and then the particle beam 3 is irradiated onto the diseased site 2a. After the irradiation to the deepest portion ends, the range shifter 8 automatically adjusts the range to extend up to the position that is shallower by a depth corresponding to the peak width than the deepest portion, and the settings for the wobbler magnets 5 and the multileaf collimator 14 are also changed; then, irradiation is carried out. Thereafter, similarly, the range shifter 8 adjusts the range and the settings for the wobbler magnets 5 and the multileaf collimator 14 are changed, so that a dose optimized as a whole for the shape of the diseased site 2a is delivered.

In the multi-layer conformal irradiation for a particle-beam treatment, in order to perform a high-accuracy particle-beam treatment as described above, it is necessary to ascertain and monitor, in each of the irradiation steps, the setting for the shape of the multileaf collimator. Accordingly, by mounting the detachable and attachable optical shape-monitoring unit 31 and the video camera 15a in the snout portion at the downstream side of the irradiation head 1, particularly in a case situated at the downstream side of the multileaf collimator and disposing in the optical shape-monitoring unit 31 the shape-monitoring mirror 32a, for monitoring the shape of the multileaf collimator 14, slanted on the beam axis, the video camera 15a shoots the reflected image of the multileaf collimator. On this occasion, the downstream-side shape of the multileaf collimator appears in the shape-monitoring mirror 32a. The image distortion (aspect ratio and the like), caused by the arrangement of the shooting system, e.g., the shape-monitoring mirror 32a, of the multileaf-collimator-shape raw image 39 shot by the video camera is corrected by the video signal processing circuit 33, so that a multileaf-collimator-shape direct-view-corresponding image 41, which is equivalent to an image as directly viewed in the beam axis, is generated.

The image processing computer 34 extracts the outline of the set shape of the multileaf collimator from the direct-view-corresponding image 41, by use of image discrimination processing such as the binarization method (1 and 0 or white and black) and displays the outline on the image monitor 17a.

Furthermore, the image processing computer 34 performs the comparison 36 between the multileaf-collimator-shape information 35a in a treatment plan and the direct-view-corresponding image 41 and then outputs the irradiation OK signal 37 or the irradiation stop signal 38, thereby making the irradiation-system control computer 9 interlock-control the emission condition of the particle-beam irradiation, so that erroneous dose administration due to erroneous setting of the multileaf collimator is avoided. As described above, by introducing the optical image shooting through the optical shape-monitoring unit 31 and the image comparison, not only can the monitoring of setting for the leaf position be performed through the leaf-position detector 25 (refer to FIG. 9) incorporated in the multileaf collimator 14, but also can the redundant, multiple ascertainment and monitoring of the multileaf-collimator shape 21 be performed even during irradiation.

In the multi-layer conformal irradiation for particle-beam irradiation, by mounting the attachable and detachable optical shape-monitoring unit 31 in the snout portion at the downstream side of the multileaf collimator, the ascertainment and the monitoring of the multileaf-collimator shape is performed. In order to suppress the range loss of the particle beam and the increase in the scattered components that are caused through mounting of the optical shape-monitoring unit 31, the shape-monitoring mirror 32a is formed by depositing aluminum on a polyimide film and disposed slanted toward the side closer to the plane perpendicular to the beam axis. The image distortion due to the shooting system, e.g., slanted disposal of the shape-monitoring mirror, is corrected by the video signal processing circuit 33. In addition, when a conventional static particle-beam irradiation is performed in which the multileaf collimator does not operate during irradiation, by removing the optical shape-monitoring unit 31, the radiation damage to the shape-monitoring mirror 32a or the video camera 15a can be reduced.

In order to suppress the dose distribution in the irradiation field defined by the multileaf collimator from being deteriorated due to the increase in a drift distance, the gradient θ, from the traveling direction of the particle beam, of the shape-monitoring mirror 32a opposing the multileaf collimator is made to be close to 90°, rather than 45°. As a result, the space, in the traveling direction of the particle beam, occupied by the optical shape-monitoring unit can be reduced. By correcting the aspect-ratio distortion in an image of the video camera that shoots the multileaf-collimator shape reflected by the shape-monitoring mirror, the video-camera image is displayed on the image monitor, as an image equivalent to the image of the multileaf-collimator shape as directly viewed in the beam-axis direction.

After the image distortion and the aspect ratio of the reflected image are corrected through image processing, the image of the multileaf-collimator shape shot by the video camera is compared with the setting, for the multileaf-collimator shape, which has been planed in a treatment-plan apparatus; in the case where the result of the comparison is inappropriate, the irradiation is interrupted; in the case where the result of the comparison is appropriate, the irradiation is carried on or made stand-by. The foregoing operation enables, even during irradiation, redundant and high-reliability ascertainment and monitoring of the shape of a multileaf collimator, without interrupting particle-beam irradiation; in consequence, a particle-beam treatment system that reduces the probability of erroneous irradiation and enables high-accuracy particle-beam treatment can be configured.

Embodiment 2

Figure 4:
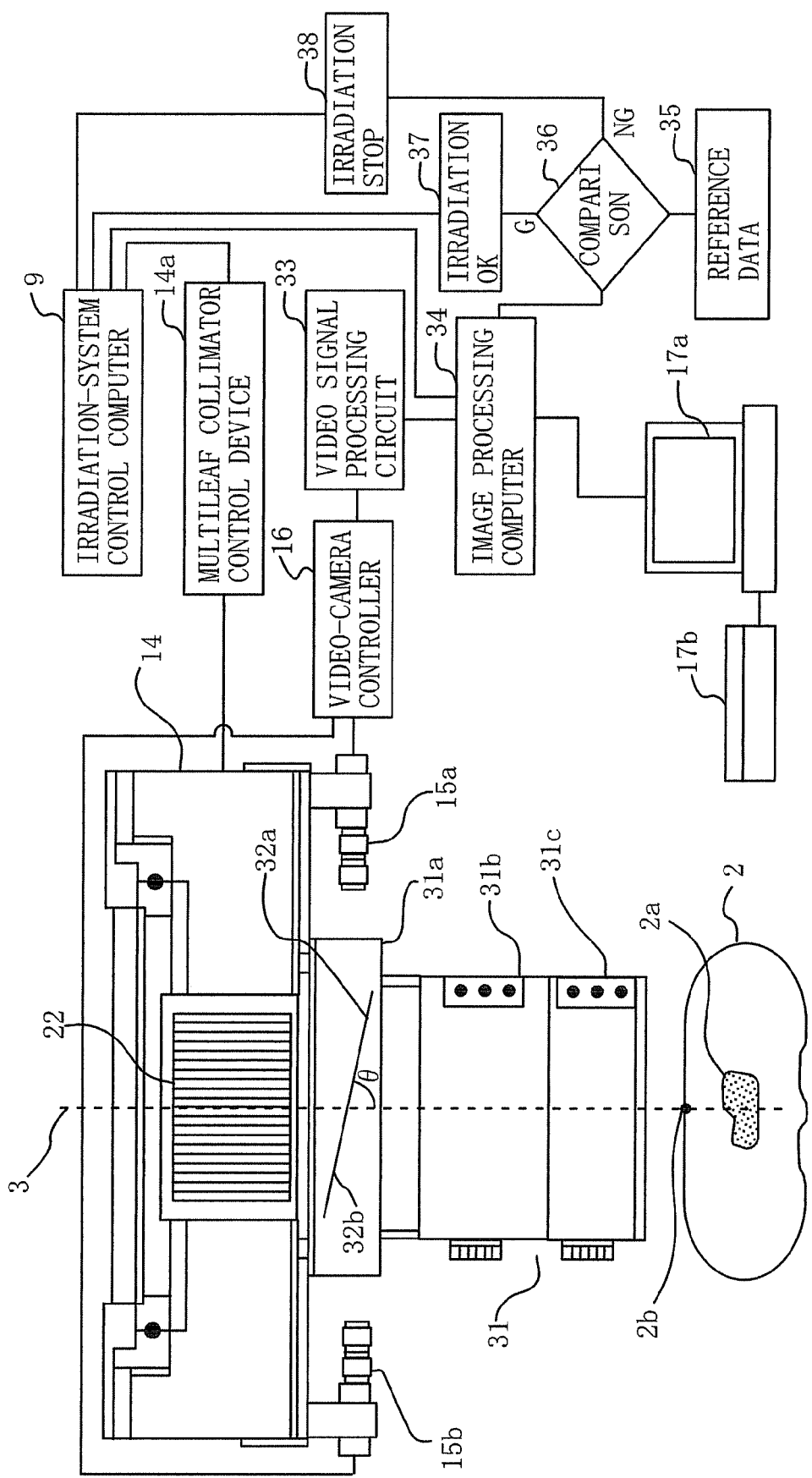
FIG. 4 is a system block diagram illustrating a multileaf collimator head unit and the control system therefor according to Embodiment 2.

In Embodiment 1, the shape of a multileaf collimator is shot by means of the shape-monitoring mirror 32a, and the video camera 15a; however, the monitoring of a patient position, which is symmetric with the multileaf collimator 14 with respect to the mirror plane, can be performed with a similar shooting system. In other words, by making the monitoring mirror a two-side mirror and utilizing the respective sides as the shape-monitoring mirror 32a and a patient-position monitoring mirror 32b, the multileaf-collimator shape and the patient position can be monitored and ascertained concurrently or in a time-division fashion. FIG. 4 is a system block diagram illustrating a multileaf collimator head unit and the control system therefor according to Embodiment 2.

Figure 5:
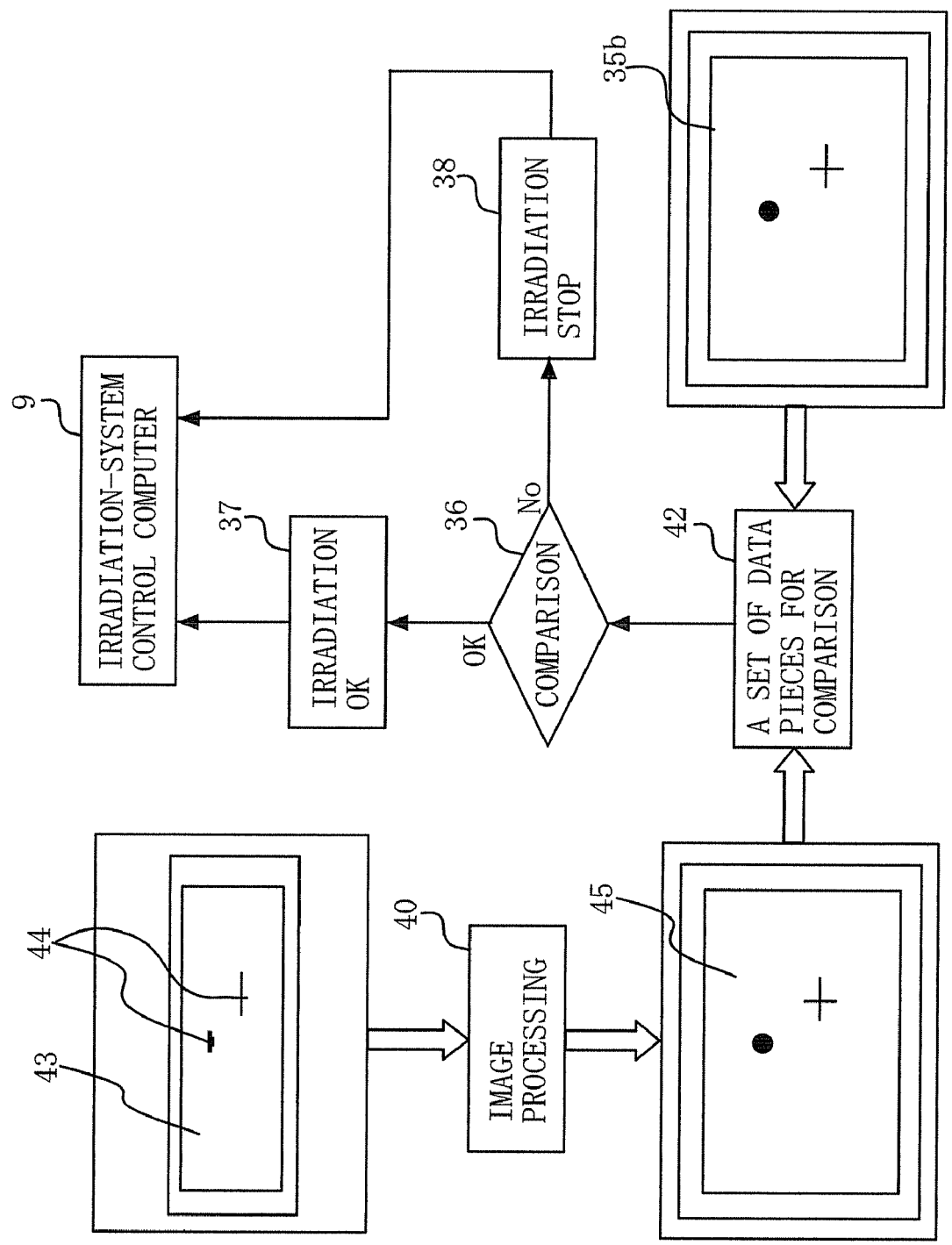
FIG. 5 is a flowchart representing a patient-position monitoring flow according to Embodiment 2.

FIG. 5 is a flowchart representing a patient-position monitoring flow according to Embodiment 2; In Embodiment 2, the steps in the flowchart, in FIG. 3, representing a collimator-shape monitoring flow are performed concurrently or in a time-division fashion. In addition, in the case the steps are concurrently performed, two systems of required apparatuses may be utilized. In Embodiment 2, the one side of a monitoring mirror serves as the shape-monitoring mirror 32a and the other side serves as the patient-position monitoring mirror 32b; an optical shape-monitoring unit is included in the optical shape-monitoring unit 31 mounted attachably and detachably in the snout portion at the downstream side of the multileaf collimator.

FIGS. 4 and 5 will mainly be explained. Reference characters 32a and 15a denote a shape-monitoring mirror and a video camera therefor, respectively, and reference characters 32b and 15b denote a patient-position monitoring mirror and a video camera therefor, respectively. Reference numeral 35 denotes reference data pieces, for the comparison, which are multileaf-collimator-shape information in a treatment plan and patient-position information. In FIG. 5, reference character 35b denotes reference data, for the comparison, which is the patient-position information. Reference numerals 42, 43, 44 and 45 denote a set of image data pieces for the comparison, a patient-position raw image, a patient-position marker, and a patient-position direct-view-corresponding image, respectively.

In FIG. 4, the shape-monitoring mirror 32a and the patient-position monitoring mirror 32b are formed, as a two-side mirror, by depositing aluminum on a single polyimide film.

Next, the operation of the particle-beam treatment system will be explained. The image reflected by the shape-monitoring mirror 32a that monitors the multileaf-collimator shape and the image reflected by the patient-position monitoring mirror 32b that opposes a patient and monitors the patient position are shot by the video cameras 15a and 15b, respectively; the distortions in the foregoing reflected images are corrected by the video signal processing circuit 33. In other words, the patient-position raw image 43, shot by the video camera 15b for monitoring the patient position, which is obtained by shooting, in the beam-irradiation direction, a patient as an irradiation subject receives image processing 40 in the video signal processing circuit 33 and corrected into the patient-position direct-view-corresponding image 45.

The corrected patient-position direct-view-corresponding image 45 is displayed on the image monitor 17a, along with the corrected multileaf-collimator-shape direct-view-corresponding image 41. On the image monitor 17a, for example, by dividing the display screen into two portions, the patient-position direct-view-corresponding image 45 and the multileaf-collimator-shape direct-view-corresponding image 41 are displayed. The image processing computer 34 records, in the patient-position direct-view-corresponding image 45 prior to irradiation, image information on an interested region, including characteristic points, e.g., a patient-position marker 44, as the patient-position information (reference data) 35*b* in a treatment plan, for the image comparison unit (comparison means) 36.

Thereafter, a set of data pieces 42 for the comparison between the patient-position direct-view-corresponding image 45 shot during particle-beam irradiation and the patient-position information (reference data) 35*b* in a treatment plan is utilized for the image comparison 36 according to the subtraction method or the like; the irradiation OK signal 37 or the irradiation stop signal 38 is outputted so as to make the irradiation-system control computer 9 interlock-control the emission condition of the particle-beam irradiation, so that erroneous dose administration due to a change in the patient position is avoided. The combination of the operation according to the flow in FIG. 5 and the operation according to the flow in FIG. 3 enables the monitoring and ascertainment of the set shape of the multileaf collimator and the patient position; therefore, during the multi-layer conformal irradiation, erroneous irradiation due to erroneous setting of a multileaf collimator and a change in a patient position can be avoided, whereby a high-reliability particle-beam treatment can be performed.

Moreover, no dead angle occurs for the patient-monitoring image shot by the optical patient-position monitoring unit; therefore, by setting an appropriate monitoring marker on the surface of a patient body, a high-accuracy patient-monitoring means can be provided. The foregoing operation can provide, even during irradiation, a redundant and high-reliability means for accurately ascertaining and monitoring a patient position, without interrupting particle-beam irradiation; in consequence, a particle-beam treatment system that reduces the probability of erroneous irradiation and enables high-accuracy particle-beam treatment can be configured.

In order to suppress the dose distribution in the irradiation field defined by the multileaf collimator from being deteriorated due to the increase in a drift distance, the gradient θ, from the traveling direction of the particle beam, of the patient-position monitoring mirror 32*b* opposing the patient is made to be close to 90°, rather than 45°. As a result, the space, in the traveling direction of the particle beam, occupied by the optical patient-position monitoring unit can be reduced. Moreover, by correcting through image processing the aspect-ratio distortion in an image of the video camera that shoots the patient position reflected by the patient-position monitoring mirror 32*b*, the video-camera image may preferably be displayed on the image monitor, as an image equivalent to the image of the patient-position as directly viewed in the beam-axis direction.

Still moreover, by providing the image processing computer 34 that extracts, by use of the binarization method (1 and 0 or white or black), the respective outlines or characteristic points from the signal for the image of the video camera that shoots the multileaf-collimator shape and the signal for the image of the video camera that shoots the patient position, the multileaf-collimator shape and the patient position may be enabled to be monitored based on the extracted outlines or characteristic points of the monitoring subject.

Embodiment 3

Figure 6:
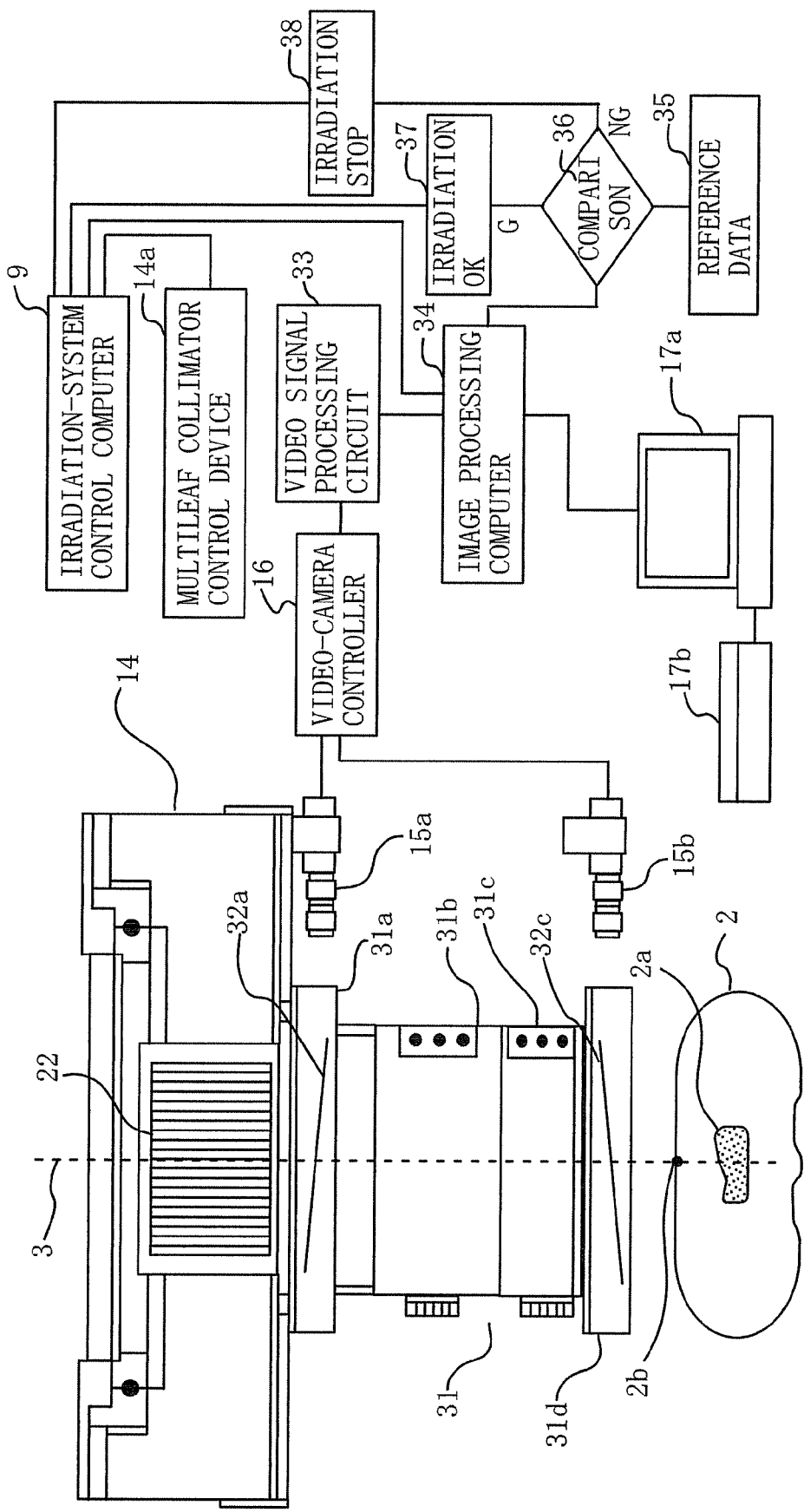
FIG. 6 is a system block diagram illustrating a multileaf collimator head unit and the control system therefor according to Embodiment 3.

FIG. 6 is a system block diagram illustrating a multileaf collimator head unit and the control system therefor according to Embodiment 3. In the case where a compensation filter (for compensating the particle-beam distribution) is mounted in the compensation filter mounting stand 31*b* of the optical shape-monitoring unit 31, or in the case where a patient collimator is mounted in the patient collimator mounting stand 31*c*, it is impossible or difficult, with Embodiment 2, to monitor and ascertain the patient position. In order to solve the foregoing problem, a patient-position monitoring mirror mounting stand 31*d* on which the patient-position monitoring mirror 32 is disposed is mounted on the front end of the optical shape-monitoring unit 31 so as to monitor and ascertain the patient position. In this case, the patient-position monitoring mirror 32*c* and the patient-position monitoring mirror mounting stand 31*d* configure an optical patient-position monitoring unit; i.e., the optical patient-position monitoring unit is mounted at the downstream side of the multileaf collimator. Additionally, the mounting position of the video camera 15*b* is moved to a position where the video camera 15*b* can shoot the patient-position image reflected by the patient-position monitoring mirror 32*c*.

As a result, even in the case where the compensation filter or the patient collimator is mounted, the patient position as well as the multileaf-collimator shape can be ascertained; therefore, during the multi-layer conformal irradiation, erroneous irradiation due to erroneous setting of the multileaf-collimator shape or a change in a patient position can be avoided, whereby a high-reliability particle-beam treatment can be performed.

Embodiment 4

Figure 7:
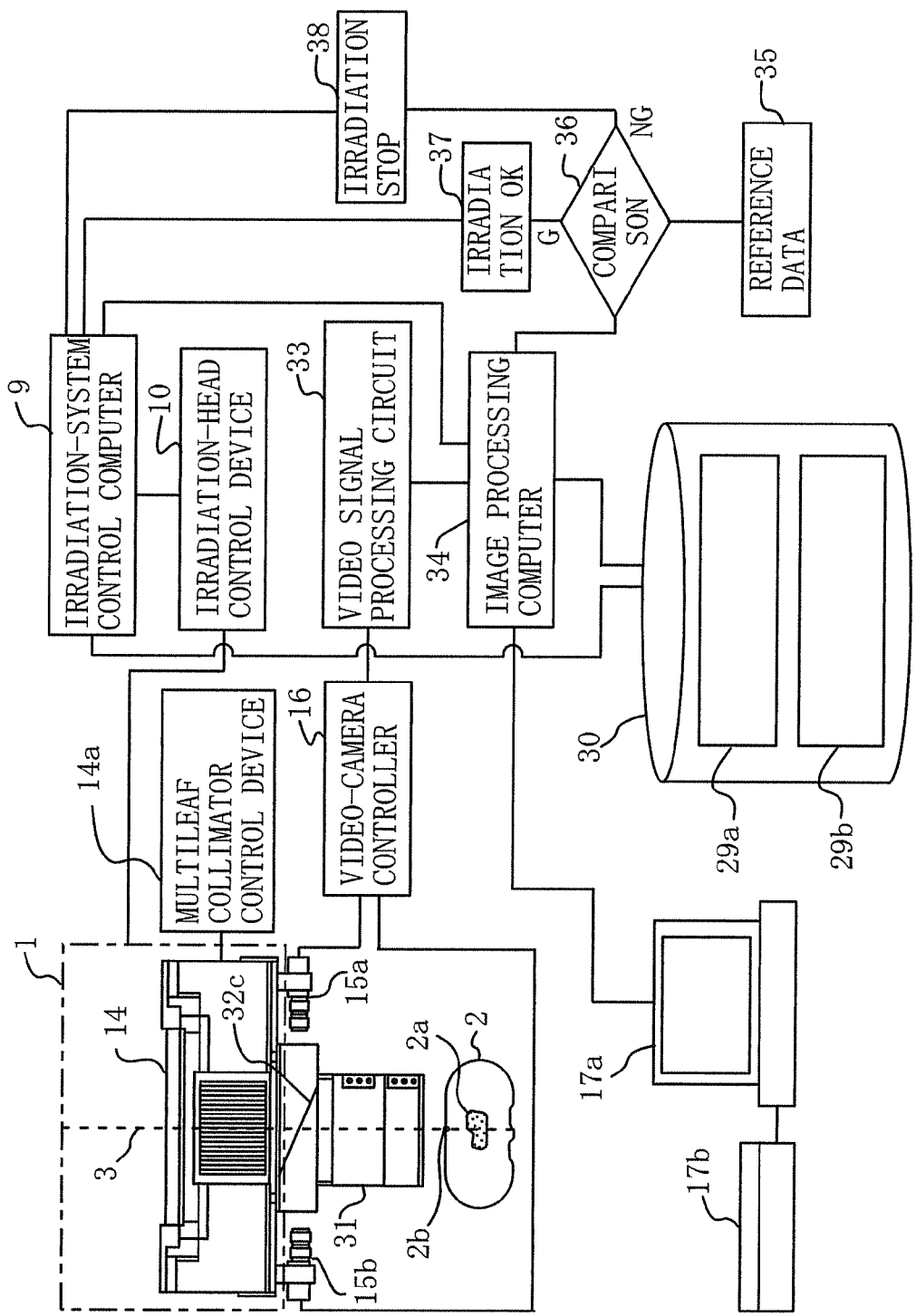
FIG. 7 is a system block diagram illustrating a multileaf collimator head unit and the control system therefor according to Embodiment 4.
Figure 8:
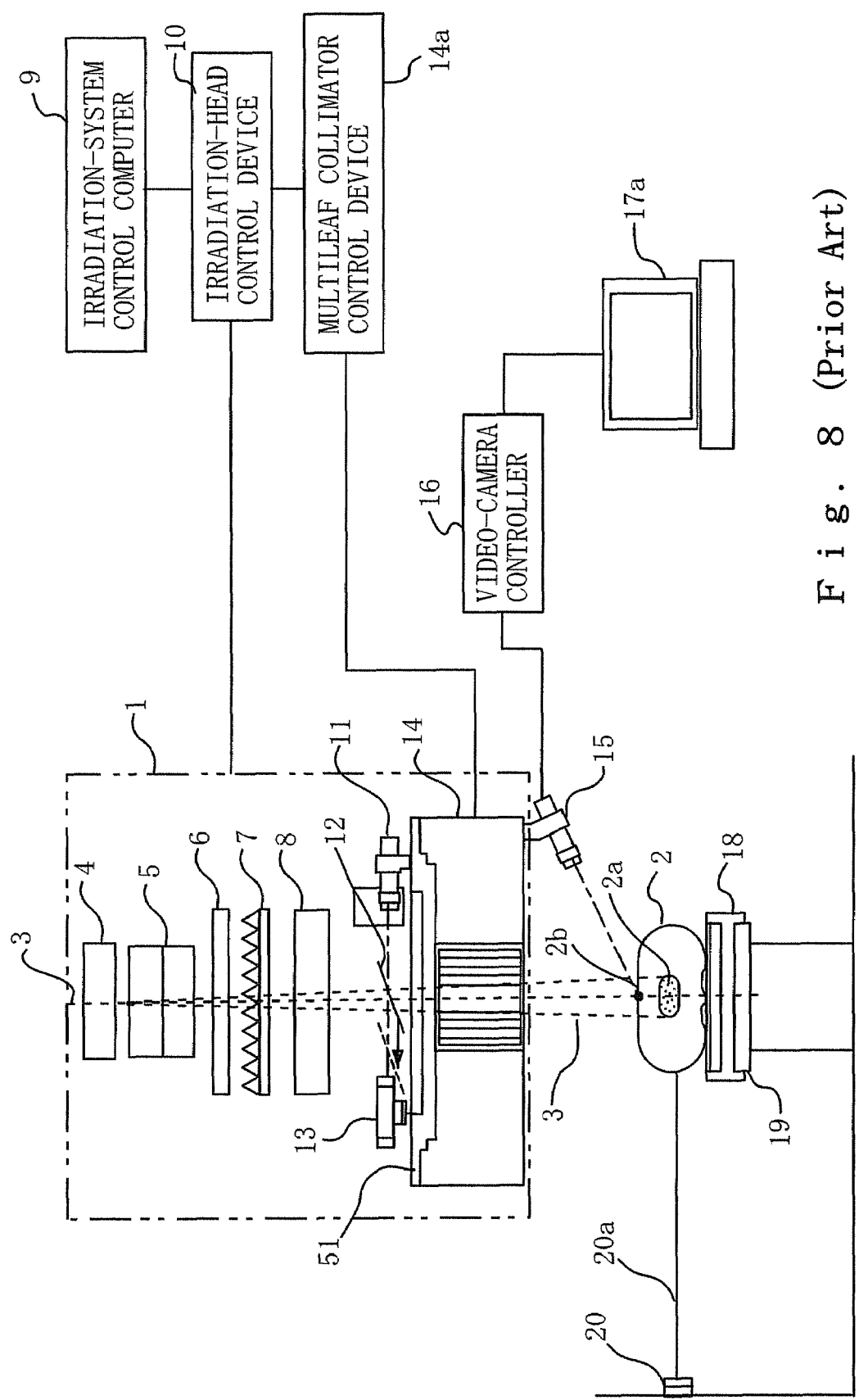
FIG. 8 is a conventional system block diagram illustrating a method of monitoring and ascertaining the shape of a multileaf collimator and a patient position in the case where a static irradiation, which has been practiced since the time before the advent of the multi-layer conformal irradiation, is performed.

FIG. 7 is a system block diagram illustrating a multileaf collimator head unit and the control system therefor according to Embodiment 4. In the multi-layer conformal irradiation, the image processing computer 34 performs the comparison 36 between the multileaf-collimator-shape information or the patient-position information that is image-corrected by the video signal processing circuit 33 and reference data 35 that is the multileaf-collimator-shape information or the patient-position information in the treatment plan, respectively. In the case where, after the start of particle-beam irradiation, the comparison result is inappropriate, the irradiation stop signal 38 is outputted, and then the particle-beam irradiation is immediately cut off.

The case that is relatively likely to occur and in which, due to an inappropriate comparison result, particle-beam irradiation is cut off is exemplified by a case where the patient position changes. In this situation, in the case where, after the cutoff, the multi-layer conformal irradiation is resumed, high-dose and low-dose regions are formed unless the patient position prior to the cutoff is reproduced. Accordingly, patient-position information 29*a* upon the start of irradiation is stored in an irradiation-condition storage medium 30 so as to be able to be referred to, as reference information, when the normality of setting for the patient position is ascertained upon the resumption of irradiation. In addition, irradiation-head device setting information 29*a* upon the start of irradiation is also stored in the irradiation-condition storage medium 30. In this case, irradiation-head devices to be set include the wobbler magnets 5, the range shifter 8, and the multileaf collimator 14; concurrently with counting through the dose monitor 4, the irradiation-system control computer 9 stores the setting conditions of the devices in the irradiation-condition storage medium 30.

After the reproducibility of the patient position is ascertained through referring to the foregoing information pieces and performing re-positioning by means of X-rays, the device conditions are set based on the irradiation-head device setting information 29*b* that has been stored during the interruption of irradiation and then the irradiation is resumed. Additionally, in order to comprehend the effects of erroneous setting for the devices of the irradiation head and a change in the patient position, during the interruption of irradiation, the patient-position information and the irradiation-head device setting information 29b during the cutoff of irradiation are stored in the irradiation-condition storage medium 30. As described above, by securely storing the irradiation-head device setting information and the patient-position information during the multi-layer conformal irradiation, the conditions of the irradiation-head device setting and the patient position during the interruption of irradiation can be comprehended; therefore, in the case where the resumption of irradiation is possible, by resuming irradiation at the time of the resumption of irradiation, the planned irradiation can be compensated, whereby high-reliability particle-beam treatment can be performed.

While the presently preferred embodiments of the present invention have been shown and described. It is to be understood that these disclosures are for the purpose of illustration and that various changes and modifications may be made without departing from the scope of the invention as set forth in the appended claims.

What is claimed is:

1. A particle-beam treatment system in which, in the case where, during particle-beam irradiation, multi-layer conformal irradiation is performed while setting of the shape of a multileaf collimator in an irradiation head is changed, the shape of the multileaf collimator is detected by a leaf-position detection mechanism, the particle-beam treatment system comprising:
   an optical shape-monitoring unit mounted attachably and detachably in the snout portion at the downstream side of the multileaf collimator, the optical shape-monitoring unit having a shape-monitoring mirror, opposing the multileaf collimator, for monitoring the shape of the multileaf collimator;
   a video camera for shooting the shape, of the multileaf collimator, which is reflected by the shape-monitoring mirror; and
   an image monitor for displaying an image of the video camera that shoots the shape of the multileaf collimator, the shape of the multileaf collimator being able to be monitored during particle-beam irradiation.

2. The particle-beam treatment system according to claim 1, wherein a gradient of the shape-monitoring mirror opposing the multileaf collimator is made close to 90°, rather than 45°, from a traveling direction of a particle beam so as to reduce the space, in the traveling direction of a particle beam, of the optical shape-monitoring unit; an aspect-ratio distortion in an image of the video camera that shoots the multileaf-collimator shape reflected by the shape-monitoring mirror is corrected through image processing; and the image of the video camera is displayed on the image monitor, as an image equivalent to the image of the multileaf-collimator shape as directly viewed in the beam-axis direction.

3. The particle-beam treatment system according to claim 1, the particle-beam treatment system comprising:
   an optical patient-position monitoring unit mounted attachably and detachably at the downstream side of the multileaf collimator, the optical shape-monitoring unit having a patient-position monitoring mirror, opposing a patient, for monitoring a patient position;
   a video camera for shooting the patient position reflected by the patient-position monitoring mirror; and
   an image monitor for displaying the respective images of the video camera that shoots the shape of the multileaf collimator and the video camera that shoots the patient position, the shape of the multileaf collimator and the patient position being able to be monitored during particle-beam irradiation.

4. The particle-beam treatment system according to claim 3, wherein the one side of the monitoring mirror serves as the shape-monitoring mirror and the other side serves as the patient-position monitoring mirror, and the optical shape-monitoring unit includes the optical patient-position monitoring unit.

5. The particle-beam treatment system according to claim 3, further comprising an image-processing means for extracting by use of a binarization method respective outlines or characteristic points from signals for images of the video camera that shoots the shape of the multileaf collimator and the video camera that shoots the patient position, wherein the multi leaf-collimator shape and the patient position are enabled to be monitored based on the respective extracted outlines or characteristic points of monitoring subjects.

6. A particle-beam treatment system in which, in the case where, during particle-beam irradiation, multi-layer conformal irradiation is performed while setting of the shape of a multileaf collimator in an irradiation head is changed, the shape of the multileaf collimator is detected by a leaf-position detection mechanism, the particle-beam treatment system comprising:
   an optical shape-monitoring unit mounted attachably and detachably in the snout portion at the downstream side of a multileaf collimator, the optical shape-monitoring unit having a shape-monitoring mirror, opposing the multileaf collimator, for monitoring the shape of the multileaf collimator;
   a video camera for shooting the multileaf-collimator shape reflected by the shape-monitoring mirror; and
   a comparison means for comparing an image of the video camera with multileaf-collimator-shape information in a treatment plan and determining whether or not the comparison result is appropriate,
particle-beam irradiation or particle-beam cutoff processing being performed depending on whether or not the comparison result is appropriate.

7. The particle-beam treatment system according to claim 6, the particle-beam treatment system comprising:
   an optical patient-position monitoring unit mounted attachably and detachably at the downstream side of the multileaf collimator, the optical shape-monitoring unit having a patient-position monitoring mirror, opposing a patient, for monitoring a patient position;
   a video camera for shooting the patient position reflected by the patient-position monitoring mirror; and
   a comparison means for comparing an image of the video camera with patient-position information in a treatment plan and determining whether or not the comparison result is appropriate,
particle-beam irradiation or particle-beam cutoff processing being performed depending on whether or not the comparison result is appropriate.

8. The particle-beam treatment system according to claim 7, wherein a gradient of the patient-position monitoring mirror opposing the patient is made close to 90°, rather than 45°, from a traveling direction of a particle beam so as to reduce the space, in the traveling direction of a particle beam, of the optical patient-position monitoring unit; an aspect-ratio distortion in an image of the video camera that shoots the patient position reflected by the patient-position monitoring mirror is corrected through image processing; and the image of the video camera is displayed on the image monitor, as an image equivalent to the image of the patient position as directly viewed in the traveling direction of a particle beam.

9. The particle-beam treatment system according to claim 7, wherein, in the case where the result of the comparison, performed by the comparison means for comparing an image of the video camera that shoots the patient position reflected by the patient-position monitoring mirror with patient-position information in a treatment plan, is inappropriate and particle-beam irradiation is interrupted, information, during the interruption, on settings for devices in the irradiation-head is stored and conditions, when particle-beam irradiation is resumed, for the devices in the irradiation-head are set by use of the information on settings for the devices, so that planned particle-beam irradiation is compensated.

* * * * *